(12) United States Patent
Fava Bekisz et al.

(10) Patent No.: US 10,532,010 B2
(45) Date of Patent: Jan. 14, 2020

(54) VOLUMIZING MASCARA COMPOSITIONS

(71) Applicant: Avon Products, Inc., Suffern, NY (US)

(72) Inventors: Collette Fava Bekisz, Bronxville, NY (US); Rahul A. Ranade, Morristown, NJ (US)

(73) Assignee: Avon Products, Inc., Suffern, NY (US)

( * ) Notice: Subject to any disclaimer, the term of this patent is extended or adjusted under 35 U.S.C. 154(b) by 79 days.

(21) Appl. No.: 14/675,818

(22) Filed: Apr. 1, 2015

(65) Prior Publication Data

US 2015/0297473 A1 Oct. 22, 2015

Related U.S. Application Data

(60) Provisional application No. 61/981,107, filed on Apr. 17, 2014.

(51) Int. Cl.
| | | |
|---|---|---|
| *A61K 8/06* | (2006.01) | |
| *A61K 8/60* | (2006.01) | |
| *A61Q 1/10* | (2006.01) | |
| *A61K 8/49* | (2006.01) | |
| *A61K 8/34* | (2006.01) | |

(52) U.S. Cl.
CPC ............ *A61K 8/062* (2013.01); *A61K 8/342* (2013.01); *A61K 8/498* (2013.01); *A61K 8/60* (2013.01); *A61Q 1/10* (2013.01)

(58) Field of Classification Search
None
See application file for complete search history.

(56) References Cited

U.S. PATENT DOCUMENTS

| | | | | |
|---|---|---|---|---|
| 5,153,046 A | * | 10/1992 | Murphy | ............... D06M 7/00 252/8.62 |
| 5,866,111 A | | 2/1999 | Felardos et al. | |
| 5,976,555 A | * | 11/1999 | Liu | ............... A61K 8/06 424/401 |
| 6,024,950 A | | 2/2000 | Hirotaka et al. | |
| 9,744,116 B2 | | 8/2017 | Bolognini et al. | |
| 2002/0187116 A1 | | 12/2002 | De la Poterie | |
| 2005/0172421 A1 | | 8/2005 | Jager-Lezer et al. | |
| 2005/0238677 A1 | | 10/2005 | Mercier et al. | |
| 2006/0130248 A1 | | 6/2006 | Pays et al. | |
| 2007/0207907 A1 | * | 9/2007 | Price | ............... A21C 3/021 492/57 |
| 2012/0052100 A1 | | 3/2012 | Ide et al. | |
| 2013/0295035 A1 | | 11/2013 | Sugimoto et al. | |
| 2015/0079016 A1 | | 3/2015 | Bolognini et al. | |

FOREIGN PATENT DOCUMENTS

| | | |
|---|---|---|
| EP | 2236128 A1 | 10/2010 |
| JP | 2005068056 A | 3/2005 |
| JP | 2006306849 A | 11/2006 |
| WO | 2013/049580 A2 | 4/2013 |
| WO | 2015039825 A1 | 3/2015 |

OTHER PUBLICATIONS

Ken Klein, "Liquid Crystals and Emulsions: A Wonderful Marriage", May 6, 2003, p. 268.
Anonymous: "Hydrogenated Tallow Fatty Acid Safety Data Sheet," retrieved from the Internet: URL:https://www.acme-hardesty.com/wp-content/uploads/Hydrogenated-Tallow-Fatty-Acid-SDS.pdf (Feb. 12, 2015).
Anonymous: "Polysorbate—Wikipedia," retrieved from the Internet: URL:https://en.wikipedia.org/wiki/Polysorbate (May 24, 2017).
Anonymous: Emulsifiers with HLB Values, pp. 1-3, retrieved from the Internet: URL:http://www.theherbarie.com/files/resource-center/formulating/Emulsifiers_HLB_Values.pdf (Apr. 29, 2011).
Anonymous: "TAGAT CH 40 TAGAT S Universal solubilizers," retrieved from the Internet: URL:http://glenncorp.com/wp-content/uploads/2013/11/DS_TAGAT_CH40_S_e-1.pdf (Nov. 1, 2009).
Supplementary European Search Report to corresponding EP Application No. 15779417.3 dated Oct. 5, 2017 (14 pages).

* cited by examiner

*Primary Examiner* — Jennifer A Berrios
(74) *Attorney, Agent, or Firm* — Brian P. McCloskey

(57) ABSTRACT

The present invention relates generally to mascara compositions that impart volume to the eyelashes while maintaining a smooth texture and high shine.

6 Claims, 1 Drawing Sheet

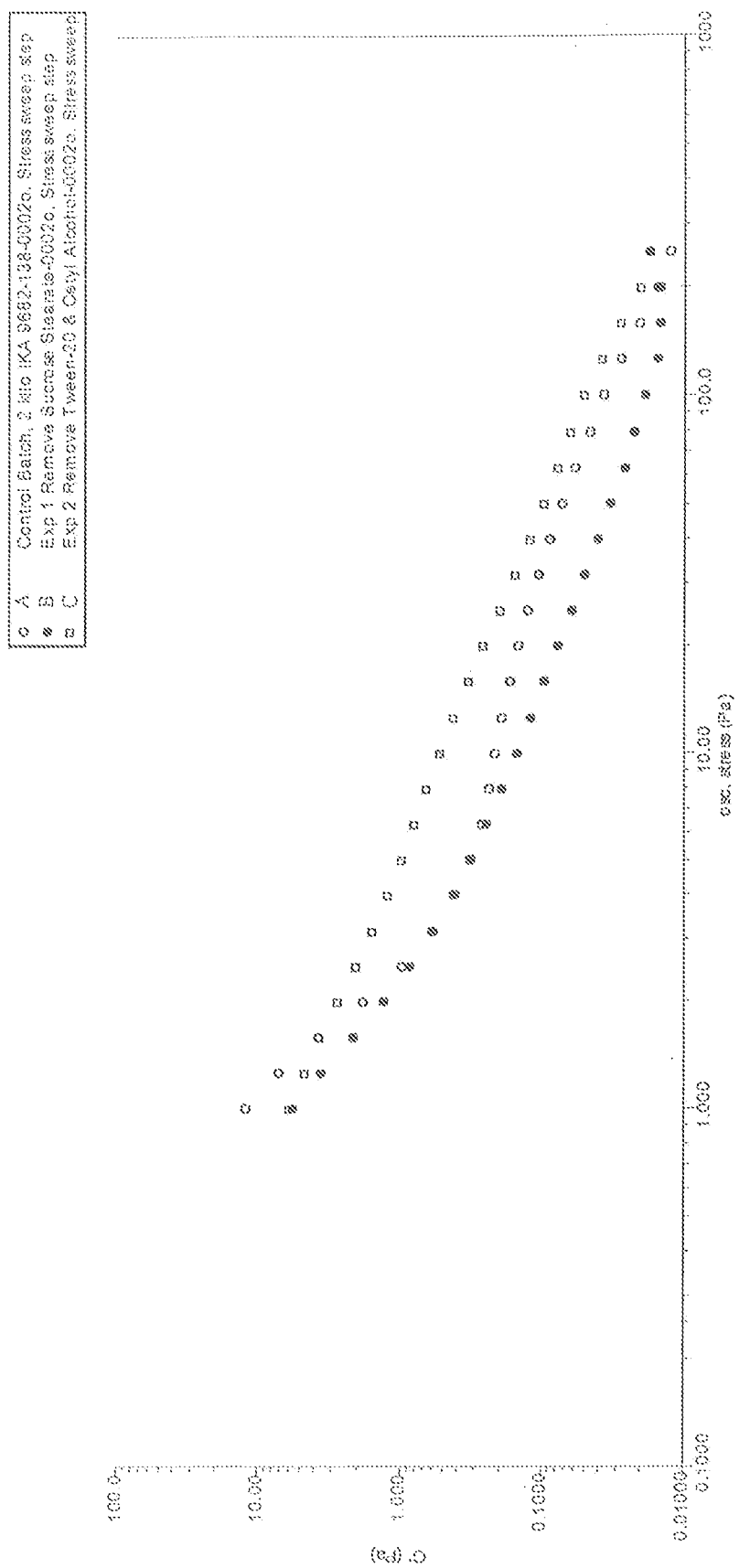

VOLUMIZING MASCARA COMPOSITIONS

CROSS-REFERENCE TO RELATED APPLICATIONS

This application claims priority to U.S. Provisional Patent Application Ser. No. 61/981,107, the entirety of which is incorporated herein for all purposes.

FIELD OF INVENTION

The present invention relates generally to mascara compositions that impart volume the eyelashes while maintaining a smooth texture and high shine.

BACKGROUND

Consumers generally apply mascara to add thickness, volume, and color to the eyelashes. Many volumizing mascaras achieve this effect through the use of high levels of waxes and/or polymeric film formers in the formulations. However, mascaras containing high amounts of waxes and/or film formers are often heavy and dull, and are difficult to apply to the eyelashes. In addition, high wax mascaras often result in clumping, leaving portions of the eyelashes stuck together rather than being separated and individually coated with the mascara.

There is therefore a need for improved mascara compositions. It is an object of the invention to provide mascara compositions that deliver volume, shine, and color to the eyelashes while maintaining a desirable rheology so that the product can be easily and smoothly applied while minimizing clumping of the eyelashes.

SUMMARY OF THE INVENTION

In accordance with the foregoing objectives and others, the present invention provides cosmetic compositions (e.g., mascara) comprising an amount of wax sufficient to provide a volumizing effect (e.g., from about 10-35% by weight) while maintaining a sufficiently low fluid rheology (e.g., a viscosity less than about 200,000 cps) such that the mascara applies evenly and without clumping to the eyelashes. It has surprisingly been found that the combination of certain medium HLB emulsifiers (e.g., saccharides derivatized with fatty chains, such as sucrose monostearate) and high HLB emulsifiers (e.g., HLB value from about 15 to about 20) allow for a high wax content (e.g., about 20-30% by weight) without compromising the smooth viscosity desired for a mascara.

In one aspect of the invention, mascara compositions are provided that comprise an oil phase, a water phase, a medium HLB emulsifier comprising a fatty derivative (e.g., ester or ether) of a disaccharide (e.g., sucrose stearate, including sucrose monostearate) in an amount sufficient to form a lamellar phase, and a high HLB emulsifier (e.g., polysorbate 20 and/or cetyl alcohol) in an amount sufficient to stabilize the lamellar phase. The medium HLB emulsifiers typically have an HLB value of between about 7 and about 15 (or between about 7 and about 14.9). The high HLB emulsifiers typically have an HLB value of between about 15 and about 20 (or between about 15.1 and about 20). Typically, the medium HLB emulsifier is different from the high HLB emulsifier. Typically, the medium HLB emulsifier has an HLB value lower than the HLB value of the high HLB value emulsifier. The mascara composition typically comprises one or more waxes (e.g., carnauba wax, beeswax, paraffin wax, ozokerite wax, silicone wax, etc.) which may be present from about 1% to about 50% by weight, but are typically present in an amount sufficient to provide a volumizing effect to the lashes, for example between about 10% and about 35% by weight (e.g., between about 20-30%, or between about 21-28%, or between about 23%-27% by weight). The mascara ideally retains a fluid viscosity even at these high wax loadings such that the composition can be readily applied to the lashes without clumping. Typically, the viscosity of the composition will be less than about 200,000 cps (e.g., less than about 150,000 cps, or less than about 100,000 cps), measured at a shear rate of $10^{-s}$ at 25° C. Typically, the mascara composition is in the form of an oil-in-water emulsion that comprises a lamellar phase. The lamellar phase may comprise, for example, from about 5% to about 95% by volume of the composition. The mascara composition may further comprise a micellar phase. The micellar phase may comprise, for example, from about 5% to about 95% by volume of the composition. The medium HLB emulsifier will typically comprise between about 0.1% and about 6% (e.g. between about 1% and about 3%) by weight of the composition and the high HLB emulsifier will typically comprise between about 0.1% and about 25% (e.g. between about 0.5% and about 15%) by weight of the composition. The mascara compositions may also further comprise a pigment (e.g., iron oxide, carbon black, etc.), and may also comprise a polymeric film former (e.g., acrylates copolymer), a thickener (e.g., hydroxyethylcellulose, xanthan gum, etc.), and other cosmetic adjuvants. The mascara is adapted for application to the eyelashes to form a film thereon which imparts a volumizing effect.

These and other aspects of the present invention will become apparent to those skilled in the art after a reading of the following detailed description of the invention, including the appended claims.

BRIEF DESCRIPTION OF THE DRAWINGS

FIG. 1 shows rheology curves for a mascara formulation of the invention (○) compared to otherwise identical compositions lacking the sucrose stearate emulsifier (●) or lacking the high HLB emulsifiers (□), when subjected to increasing amounts of oscillatory stress.

DETAILED DESCRIPTION

All terms used herein are intended to have their ordinary meaning unless otherwise provided. All ingredient amounts provided herein are by weight percent of the total composition unless otherwise indicated. It will be understood that the total of all weight percentages and the total volume percentages in a given composition will not exceed 100%.

The term "consisting essentially of" is intended to include only those components that do not materially alter the basic and novel features of the inventive compositions, including without limitation, the stability of the lamellar phase, and the fluid rheology of the composition.

The compositions of the invention generally comprise an oil-in-water emulsion. The emulsion typically comprises an oil phase in an amount from about 5-95% by weight and a water phase in an amount from about 5-95% by weight, and optionally a particulate phase (e.g., pigments, lakes, fillers, polymeric particles, etc.) which may, for example, comprise from about 1-25% by weight of the emulsion. The compositions include a medium Hydrophilic-Lipophilic Balance (HLB) emulsifier comprising a saccharide derivatized with a fatty chain. Without wishing to be bound by any theory, it is believed that the medium HLB emulsifier is present in an amount sufficient to form a lamellar phase. The compositions also include a high HLB emulsifier. Without being bound by theory, it is also believed that the high HLB emulsifier is present in an amount sufficient to stabilize a lamellar phase. The compositions of the invention are contemplated to be useful for any form of cosmetics, and are particularly useful as mascara compositions. The compositions typically also comprise one or more waxes sufficient to provide a volumizing effect, for example, to the eyelashes, while maintaining a fluid viscosity.

Without wishing to be bound by any particular theory, it is believed that the lamellar phase results in a smooth mascara with a low viscosity. The high HLB emulsifier is believed to stabilize the emulsion by preventing coalescence of the oil droplets, thereby preventing an increase in viscosity. It is also believed that as a result, a higher wax content can be incorporated into the composition, such as a mascara composition, thereby adding volume and shine to the eyelashes without causing an unacceptable increase in viscosity that can cause unevenness and clumping.

Medium HLB emulsifiers (e.g., sucrose monostearate) may be present in the compositions of the invention in an amount sufficient to form a lamellar phase. In some embodiments, the medium HLB emulsifier is present in an amount between about 0.1% and about 6% by weight, or from about 0.2% to about 5% by weight, or from about 0.3% to about 4% by weight, or from about 0.4% to about 5% by weight, or from about 0.5% to about 5% by weight of the composition. In one embodiment, the medium HLB emulsifier is present in an amount of about 0.5%, about 1%, about 2%, or about 3% by weight of the composition.

In one embodiment, the composition comprises a lamellar phase. In another embodiment, the composition comprises a micellar phase. In one embodiment, the composition comprises a lamellar phase and a micellar phase. The ratio of the volume % of the lamellar phase to the volume % of the micellar phase may be, without limitation, from about 99:1 to about 1:99, or from about 50:1 to about 1:50, or from about 25:1 to about 1:25, or from about 10:1 to about 1:10, or from about 5:1 to about 1:5, or from about 2:1 to about 1:2, or from about 3:2 to about 2:3, or, in one embodiment, about 1:1.

Suitable medium HLB emulsifiers include fatty derivatives (e.g., esters or ethers) of a monosaccharide, disaccharide, or trisaccharide, in an amount sufficient to form a lamellar phase. Typically the medium HLB emulsifiers comprise a fatty ester or ether of a disaccharide. Preferably, the medium HLB emulsifier comprises a $C_{12}$-$C_{22}$ (optionally branched or straight-chain) fatty group (e.g., hydrocarbon). The fatty chains may be selected from, without limitation, $C_{12}$ hydrocarbons (e.g., laurate), $C_{14}$ hydrocarbons (e.g., myristate), $C_{16}$ hydrocarbons (e.g., palmitate), $C_{18}$ hydrocarbons (e.g., stearate), $C_{20}$ hydrocarbons (e.g., eicosanoate), $C_{22}$ hydrocarbons (e.g., decosanoate), etc. The saccharide component may comprise monosaccharides, disaccharides, and trisaccharaides, which may for example, be composed of fructose, glucose, galactose, mannose, rhamose, and/or xylopyranose monomers, alone or as optionally mixed dimers or trimers. In one embodiment, the emulsifier comprises a disaccharide component. The disaccharide may, for example, have as each sugar residue of the disaccharide a monomer of fructose, glucose, and/or galactose. In some embodiments, the disaccharide is selected from sucrose, lactulose, lactose, trehalose, cellubiose, or maltose, or derivatives of a disaccharide. The medium HLB emulsifier may comprise a mono-ester, a di-ester, tri-ester, etc. of the saccharide, but typically comprises a mono-ester, at least in such amounts that the HLB value of the emulsifier is between about 7 and about 15. In one embodiment, the medium HLB emulsifier comprises a mono-ester of a disaccharide. In another embodiment, the medium HLB emulsifier comprises sucrose monostearate. In one embodiment, the sucrose monostearate containing emulsifier has an HLB value of 14.5. A suitable sucrose stearate emulsifier is available from Croda as CRODESTA F160. In another embodiment, the sucrose monostearate containing emulsifier is CRODESTA F160.

In various embodiments, the medium HLB emulsifier will have an HLB value between 7-15, or between 7-14.9, or between 8-15, or between 9-15, or between 10-15, or between 11-15, or between 12-15, or between 13-15, or between 13-15.

The compositions of the invention typically comprise high HLB emulsifiers. In some embodiments, the compositions comprise high HLB emulsifiers in an amount between about 0.1% and about 25% by weight, or between about 0.3% to about 20% by weight, or between about 0.5% and about 15% by weight, or between about 1% and about 12% by weight, or between about 2% and about 10% by weight, or between about 3% and about 8% by weight of the composition.

High HLB emulsifiers contemplated as useful in the compositions of the invention typically have an HLB value of between about 15 and about 20. In one embodiment, the high HLB emulsifier has an HLB value between 15.1-20. In one embodiment, the high HLB emulsifier has an HLB value greater than the HLB value of the medium HLB emulsifier. Suitable high HLB emulsifiers, with their approximate HLB values in parentheses, include, without limitation, polysorbate-20 (16.7), cetyl alcohol (15-16), isosteareth-20 (15), PEG-60 almond glycerides (15), polysorbate-80 (15), PEG-20 methyl glucose sesquistearate (15), ceteareth-20 (15.2), oleth-20 (15.3), steareth-20 (15.3), steareth-21 (15.5), ceteth-20 (15.7), isoceteth-20 (15.7), laureth-23 (16.9), PEG-100 stearate (18.8), steareth-100 (18.8), PEG-80 sorbitan laurate (19.1), isostearic acid (15-16), lauric acid (16), linoleic acid (16), oleic acid (17), ricinoleic acid (16), decyl alcohol (15), stearyl alcohol (15-16), pine oil (16), polyethylene wax (15), and tricresyl phosphate (17). In one embodiment, the high HLB emulsifier comprises polysorbate-20 and/or cetyl alcohol. In one embodiment, the high HLB emulsifier is not a fatty derivative of a saccharide, or is not a fatty ester or ether of a saccharide, or is not a fatty ester or ether of a disaccharide, or is not a sucrose stearate, or is not a sucrose monostearate.

Additional suitable medium HLB and high HLB emulsifiers are provided in the INCI Ingredient Dictionary and Handbook, $12^{th}$ Edition (2008), the disclosure of which is hereby incorporated by reference.

The mascara compositions of the invention typically comprise one or more waxes which may be present from about 1% to about 50% by weight, but are typically present in an amount sufficient to provide a volumizing effect to the eyelashes. In some embodiments, the one or more waxes are present in amount between about 10% and about 35% by weight, or between about 15% and about 30% by weight of the composition. More typically, the compositions comprise one or more waxes in an amount between about 20% and about 30% by weight, between about 21% and about 28% by weight, or between about 23% and about 27% by weight of the composition.

Any suitable waxes may be used in the compositions of the invention, and may comprise natural, mineral and/or synthetic waxes. Natural waxes include those of animal origin (e.g., beeswax, spermaceti, lanolin, and shellac wax) and those of vegetable origin (e.g., carnauba, candelilla, bayberry, and sugarcane wax). Mineral waxes include, without limitation ozokerite, ceresin, montan, paraffin, microcrystalline, petroleum, and petrolatum waxes. Synthetic waxes include, for example, polyethylene glycols such as PEG-18, PEG-20, PEG-32, PEG-75, PEG-90, PEG-100, and PEG-180 which are sold under the tradename CARBOWAX® (The Dow Chemical Company). Mention may be made of the polyethylene glycol wax CARBOWAX 1000 which has a molecular weight range of 950 to 1,050 and a melting point of about 38° C., CARBOWAX 1450 which has a molecular weight range of about 1,305 to 1,595 and a melting point of about 56° C., CARBOWAX 3350 which has a molecular weight range of 3,015 to 3,685 and a melting point of about 56° C., and CARBOWAX 8000 which has a molecular weight range of 7,000 to 9,000 and a melting point of about 61° C.

Suitable synthetic waxes also comprise Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated) with melting points ranging from 80° C. to 132° C. Commercially available ethylene-α-olefin copolymer waxes include, for example, those sold under the tradename PETROLITE® Copolymers (Baker Hughes Incorporated) with melting points ranging from 95° C. to 115° C.

Other suitable waxes include silicone waxes, including alkyl silicones, such as alkyl dimethicone and alkyl methicone waxes.

In one embodiment, one or more waxes is selected from the group consisting of carnauba wax, beeswax, paraffin wax, and combinations thereof. Some waxes may serve as emulsifiers that can be used in addition to or in place of (in whole or in part) the high HLB emulsifier component. For example, carnauba wax may have an HLB value of about 15.

The mascara compositions of the invention ideally retain a fluid viscosity, even at high wax loadings (e.g., 20-30% by weight, or 25-30% by weight, etc.), such that the compositions can be smoothly and evenly applied to the eyelashes without clumping. Typically, the viscosity of the composition will be less than about 200,000 cps, measured at a shear rate of 10'. In some embodiments, the viscosity of the composition is less than about 180,000 cps, less than about 160,000 cps, less than about 140,000 cps, less than about 120,000 cps, or less than about 100,000 cps, as measured at a shear rate of $10^{-s}$.

Typically, the compositions of the invention comprise an oil-in-water emulsion. The emulsions typically further comprise a lamellar phase. The oil phase of the emulsion may comprise any suitable oils, including, without limitation, vegetable oils; fatty acid esters; fatty alcohols; isoparaffins such as isododecane and isoeicosane; hydrocarbon oils such as mineral oil, petrolatum, and polyisobutene; polyolefins and hydrogenated analogs thereof (e.g., hydrogenated polyisobutene); natural or synthetic waxes; silicone oils such as dimethicones, cyclic silicones, and polysiloxanes; and the like. The oil phase may comprise a singular oil or mixtures of different oils.

Suitable ester oils include fatty acid esters. Special mention may be made of those esters commonly used as emollients in cosmetic formulations. Such esters will typically be the esterification product of an acid of the form $R_4(COOH)_{1-2}$ with an alcohol of the form $R_5(OH)_{1-3}$ where $R_4$ and $R_5$ are each independently linear, branched, or cyclic hydrocarbon groups, optionally containing unsaturated bonds (e.g., from 1-6 or 1-3 or 1), and having from 1 to 30 (e.g., 6-30 or 8-30, or 12-30, or 16-30) carbon atoms, optionally substituted with one or more functionalities including hydroxyl, oxa, oxo, and the like. Preferably, at least one of $R_4$ and $R_5$ comprises at least 8, or at least 10, or at least 12, or at least 16 or at least 18 carbon atoms, such that the ester oil comprises at least one fatty chain. The esters defined above will include, without limitation, the esters of mono-acids with mono-alcohols, mono-acids with diols and triols, di-acids with mono-alcohols, and tri-acids with mono-alcohols.

Suitable fatty acid esters include, without limitation, butyl isostearate, butyl oleate, butyl octyl oleate, cetyl palmitate, ceyl octanoate, cetyl laurate, cetyl lactate, cetyl isononanoate, cetyl stearate, diisostearyl fumarate, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisopropyl dimerate, triisostearyl trilinoleate, octodecyl stearoyl stearate, hexyl laurate, hexadecyl isostearate, hexydecyl laurate, hexyldecyl octanoate, hexyldecyl oleate, hexyldecyl palmitate, hexyldecyl stearate, isononyl isononanaote, isostearyl isononate, isohexyl neopentanoate, isohexadecyl stearate, isopropyl isostearate, n-propyl myristate, isopropyl myristate, n-propyl palmitate, isopropyl palmitate, hexacosanyl palmitate, lauryl lactate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl lactate, stearyl octanoate, stearyl heptanoate, stearyl stearate, tetratriacontanyl stearate, triarachidin, tributyl citrate, triisostearyl citrate, tri-$C_{12-13}$-alkyl citrate, tricaprylin, tricaprylyl citrate, tridecyl behenate, trioctyldodecyl citrate, tridecyl cocoate, tridecyl isononanoate, glyceryl monoricinoleate, 2-octyldecyl palmitate, 2-octyldodecyl myristate or lactate, di(2-ethylhexyl)succinate, tocopheryl acetate, and the like.

Other suitable esters include those wherein $R_5$ comprises a polyglycol of the form H—(O—CHR*—CHR*)$_n$— wherein R* is independently selected from hydrogen or straight chain $C_{1-12}$ alkyl, including methyl and ethyl, as exemplified by polyethylene glycol monolaurate.

Salicylates and benzoates are also contemplated to be useful esters in the compositions of the invention. Suitable salicylates and benzoates include esters of salicylic acid or benzoic acid with an alcohol of the form $R_6OH$ where $R_6$ is a linear, branched, or cyclic hydrocarbon group, optionally containing unsaturated bonds (e.g., one, two, or three unsaturated bonds), and having from 1 to 30 carbon atoms, typically from 6 to 22 carbon atoms, and more typically from 12 to 15 carbon atoms. Suitable salicylates include, for example, octyl salicylate and hexyldodecyl salicylate, and benzoate esters including $C_{12-15}$ alkyl benzoate, isostearyl benzoate, hexyldecyl benzoate, benzyl benzoate, and the like.

Other suitable esters include, without limitation, polyglyceryl diisostearate/IPDI copolymer, triisostearoyl polyglyceryl-3 dimer dilinoleate, polyglycerol esters of fatty acids, and lanolin, to name but a few.

The oil may also comprise a volatile or non-volatile silicone oil. Suitable silicone oils include linear or cyclic silicones such as polyalkyl- or polyarylsiloxanes, for example, comprising alkyl groups having from 1 to 16 carbon atoms. Representative silicone oils include, for example, caprylyl methicone, stearyl dimethicone, cyclomethicone, cyclopentasiloxane decamethylcyclopentasiloxane, decamethyltetrasiloxane, diphenyl dimethicone, dodecamethylcyclohexasiloxane, dodecamethylpentasiloxane, heptamethylhexyltrisiloxane, heptamethyloctyltrisiloxane, hexamethyldisiloxane, methicone, methyl-phenyl polysiloxane, octamethylcyclotetrasiloxane, octamethyltrisiloxane, perfluorononyl dimethicone, polydimethylsiloxanes, amodimethicone, dimethiconol, dimethicone copolyol, and combinations thereof. The silicone oil will typically, but not necessarily, have a viscosity of between about 5 and about 3,000 centistokes (cSt), preferably between 50 and 1,000 cSt measured at 25° C.

In one embodiment, the silicone oil comprises phenyl groups, as is the case for a silicone oil such as methylphenylpolysiloxane (INCI name diphenyl dimethicone), commercially available from Shin Etsu Chemical Co under the name including F-5W, KF-54 and KF-56. Diphenyl dimethicones have good organic compatibility and may impart film-forming characteristics to the product. Further, the presence of phenyl groups increases the refractive index of the silicone oil and thus may contribute to high gloss of product if desired. In one embodiment, the silicone oil will have a refractive index of at least 1.3, preferably at least 1.4, more preferably at least 1.45, and more preferred still at least 1.5, when measured at 25° C. Another suitable phenyl-functionalized silicone oil has the INCI name phenyltrimethicone and is sold under the trade name DC 556 by Dow Corning. DC 556 has a refractive index of about 1.46. In one embodiment, the silicone oil is a fluorinated silicone, such as a perfluorinated silicone (i.e., fluorosilicones). Fluorosilicones are advantageously both hydrophobic and oleophobic and thus contribute to a desirable slip and feel of the product. Fluorosilicones can be gelled with behenyl behenate if desired. One suitable fluorosilicone is a fluorinated organo-functional silicone fluid having the INCI name perfluorononyl dimethicone. Perfluorononyl dimethicone is commercially available from Pheonix Chemical under the trade name PECOSIL®.

The compositions may also comprise hydrocarbon oils. Exemplary hydrocarbon oils comprise straight or branched chain paraffinic hydrocarbons having from 5 to 80 carbon atoms, typically from 8 to 40 carbon atoms, and more typically from 10 to 16 carbon atoms, including but not limited to, pentane, hexane, heptane, octane, nonane, decane, undecane, dodecane, tetradecane, tridecane, and the like. Some useful hydrocarbon oils are highly branched aliphatic hydrocarbons, including $C_{8-9}$ isoparaffins, $C_{9-11}$ isoparaffins, $C_{12}$ isoparaffin, $C_{29-49}$ isoparaffins and the like. Special mention may be made of the isoparaffins having the INCI names isohexadecane, isoeicosane, and isododecane (IDD).

Also suitable as hydrocarbon oils are poly-alpha-olefins, typically having greater than 20 carbon atoms, including (optionally hydrogenated) $C_{24-28}$ olefins, $C_{30-45}$ olefins, polyisobutene, hydrogenated polyisobutene, hydrogenated polydecene, polybutene, hydrogenated polycyclopentane, mineral oil, pentahydrosqualene, squalene, squalane, and the like. The hydrocarbon oil may also comprise higher fatty alcohols, such as oleyl alcohol, octyldodecanol, and the like.

Other suitable oils include, without limitation, castor oil, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, avocado oil, camellia oil, macadamia nut oil, turtle oil, mink oil, soybean oil, grape seed oil, sesame oil, maize oil, rapeseed oil, sunflower oil, cottonseed oil, jojoba oil, peanut oil, olive oil, and combinations thereof.

The water or aqueous phase of the emulsion may comprise one or more alcohols or polyhydric alcohols, such as, without limitation, lower ($C_{1-6}$) alcohols such as ethanol, and isopropyl alcohol, or humectants such as $C_{3-8}$ glycols, including glycerin, propylene glycol, butylene glycol, pentylene glycol, neopentyl glycol, and caprylyl glycol. The water or aqueous phase may also comprise a cosmetically acceptable ester such as butyl acetate or ethyl acetate; ketones such as acetone or ethyl methyl ketone; or the like. These components if present, may be included in an amount of about 25% or less by weight of the composition and in some embodiments are present in an amount of less than about 15%, less than about 10%, or less than about 5% by weight of the composition.

The water or aqueous phase of the oil-in-water emulsion will typically comprise from about 25% to about 95% of the emulsion, while the oil phase will typically comprise from about 5% to about 75% of the emulsion. All ratios within the above limits are also contemplated. For example, the water or aqueous phase may comprise about 25%, about 30%, about 35%, about 40%, about 45%, about 50%, about 55%, about 60%, about 65%, about 70%, about 75%, about 80%, about 85%, about 90% of the emulsion, or any other value within this range. Similarly, the oil phase may comprise about 10%, about 15%, about 20%, about 25%, about 30%, about 35%, about 40%, about 45%, about 50%, about 55%, about 60%, about 65%, about 70%, or about 75% of the emulsion, or any other value within this range.

The mascara compositions of the invention may also comprise colorants, such as pigments and lakes. In one embodiment, the compositions comprise a pigment, such as iron oxide and/or carbon black. Additional suitable pigments include inorganic pigments include, including, not limited to, inorganic oxides and hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO) and iron hydroxides including red iron oxide, yellow iron oxide and black iron oxide, titanium dioxide, titanium lower oxides, zirconium oxides, chromium oxides, chromium hydroxides, manganese oxides, manganese hydroxides, cobalt oxides, cobalt hydroxides, cerium oxides, cerium hydroxides, nickel oxides, nickel hydroxides, zinc oxides and zinc hydroxides and composite oxides and composite hydroxides such as iron titanate, cobalt titanate and cobalt aluminate and the like. In some embodiments, the inorganic oxide particles may be selected from silica, alumina, zinc oxide, iron oxide and titanium dioxide particles, and mixtures thereof. In one embodiment, the pigments have a particle size from 5 nm to 100 microns, or from 5 nm to 25 microns, or from 10 nm to 10 microns. In some embodiments, the particle size (median) will be less than bout 5 microns or less than 1 micron.

Additional exemplary color additive lakes include, for example: D&C Red No. 19 (e.g., CI 45170, CI 73360 or CI 45430); D&C Red No. 9 (CI 15585); D&C Red No. 21 (CI 45380); D&C Orange No. 4 (CI 15510); D&C Orange No. 5 (CI 45370); D&C Red No. 27 (CI 45410); D&C Red No. 13 (CI 15630); D&C Red No. 7 (CI 15850:1); D&C Red No. 6 (CI 15850:2); D&C Yellow No. 5 (CI 19140); D&C Red No. 36 (CI 12085); D&C Orange No. 10 (CI 45475); D&C Yellow No. 19 (CI 15985); FD&C Red #40 (CI #16035); FD&C Blue #1 (CI #42090); FD&C Yellow #5 (CI #19140); or any combinations thereof.

The pigments may be optionally surface treated, for example, to make the particles more hydrophobic or more dispersible in a vehicle. The surface of the particles may, for example, be covalently or ionically bound to an organic molecule or silicon-based molecule or may be absorbed thereto, or the particle may be physically coated with a layer of material. The surface treatment compound may be attached to the particle through any suitable coupling agent, linker group, or functional group (e.g., silane, ester, ether, etc). The compound may comprise a hydrophobic portion which may be selected from, for example, alkyl, aryl, allyl, vinyl, alkyl-aryl, aryl-alkyl, organosilicone, di-organosilicone, dimethicones, methicones, polyurethanes, silicone-polyurethanes, and fluoro- or perfluoro-derivatives thereof. Other hydrophobic modifiers include, but are not limited, lauroyl lysine, Isopropyl Titanium Triisostearate (ITT), ITT and Dimethicone (ITT/Dimethicone) cross-polymers, ITT and Amino Acid, ITT/Triethoxycaprylylsilane Crosspolymer, waxes (e.g., carnauba), fatty acids (e.g., stearates), HDI/Trimethylol Hexylactone Crosspolymer, PEG-8 Methyl. Ether Triethoxysilane, aloe, jojoba ester, lecithin, perfluoroalcohol phosphate, and Magnesium Myristate (MM). In other embodiments, the pigments may be surface treated with galactoarabinose or glyceryl rosinate. In another embodiment, the pigments may be surface treated with Disodium Stearoyl Glutamate (and) Aluminum Dimyristate (and) Triethoxycaprylysilane.

The compositions of the invention typically comprise a film former, and in particular, a polymeric film former. The term polymeric film former may be understood to indicate a polymer which is capable, by itself or in the presence of at least one auxiliary film-forming agent, of forming a continuous film which adheres to a surface and functions as a binder for the particulate material. Suitable polymeric film formers include, without limitation, acrylic polymers or co-polymers, (meth)acrylates, alkyl(meth)acrylates, polyolefins, polyvinyls, polacrylates, polyurethanes, silicones, polyamides, polyethers, polyesters, fluoropolymers, polyethers, polyacetates, polycarbonates, polyamides, polyimides, rubbers, epoxies, formaldehyde resins, organosiloxanes, dimethicones, amodimethicones, dimethiconols, methicones, silicone acrylates, polyurethane silicones copolymers, cellulosics, polysaccharides, polyquaterniums, and the like. Suitable film formers include those listed in the Cosmetic Ingredient Dictionary and Handbook, 12$^{th}$ Edition (2008), the disclosure of which is hereby incorporated by reference.

Suitable silicone acrylate copolymers include those comprising a poly(alkyl)acrylate backbone and a dimethicone polymer grafted to an alkyl ester side chain, such as the commercially available film former Cyclopentasiloxane (and) Acrylates/Dimethicone Copolymer (KP-545, Shin-Etsu Chemical Co., Ltd) and Methyl Trimethicone (and) Acrylates/dimethicone Copolymer (KP-549, Shin-Etsu Chemical Co., Ltd.)

Additional suitable polymeric film formers include, without limitation, Amino Bispropyl Dimethicone, Aminopropyl Dimethicone, Amodimethicone, Amodimethicone Hydroxystearate, Behenoxy Dimethicone, $C_{30-45}$ Alkyl Dimethicone, $C_{24-28}$ Alkyl Dimethicone, $C_{30-45}$ Alkyl Methicone, Cetearyl Methicone, Cetyl Dimethicone, Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone. Particularly preferred are silicone polymers, including Methicone (as described by CTFA Monograph No. 1581, which is incorporated herein by reference), Dimethicones (as described by CTFA Monograph No. 840, which is incorporated herein by reference) and Amodimethicones as described by CTFA Monograph No. 189, which is incorporated herein by reference). In some embodiments, the film former comprises a hydrophobic film forming polymer, such as hydroxyethylcellulose or other cellulosics, PVP, and polyvinyl alcohol. Film forming polymers may be present in an amount between about 0.1% to about 15% by weight of the composition.

The compositions of the invention may also comprise a thickener, such as, for example, a polysaccharide thickener. Suitable polysaccharide thickeners include, without limitation, natural vegetable gums, such as, Agar, alginic acid, sodium alginate, and Carrageenan, gum Arabic, gum ghatti, gum tragacanth, Karava gum, gaur gum, locust bean gum, beta-glucans, Chicle gum, Dammar gum, Glucomannan, Mastic gum, *Psyllium* seed husks, Spruce gum, Tara gum, Gellan gum, and xanthan gum; or synthetic cellulosic thickeners such as carboxymethylcellulose, hydroxyethylcellulose, hydroxypropeylcellulose, hydroxypropylmethyl cellulose, and the like. In other embodiments, the thickener may comprise a non-polysaccharide thickener. For example, polymers and copolymers of acrylic acid, including Acrylates Copolymer (INCI) are contemplated to be suitable. The composition may also comprise silica, acrylic acid polymers, hydrated magnesium and aluminium silicates, or calcium silicates, or the like. When present, thickeners may comprise from about 0.1% to about 15% by weight of the composition, more typically from about 1% to about 5% by weight of the composition.

In some embodiments, the compositions are substantially free of clay, talc, and/or bentonite, by which is meant that they are either absent or present in such a low level as to not have a material effect on the stability or rheology of the emulsion. In some embodiments, clays, talc, and bentonite, if present, will comprise less than about 0.5%, or less than about 0.2%, or less than about 0.1% by weight of the emulsion.

Various fillers and additional components may be added to the compositions. Fillers may be present in an amount between about 0.1% and about 20% by weight of the composition, more typically between about 0.1% and about 10% by weight of the composition. Suitable fillers include, without limitation, silica, treated silica, zinc stearate, mica, kaolin, Nylon powders such as Orgasol®, polyethylene powder, PTFE (e.g.,) Teflon®, powders, starch, boron nitride, copolymer microspheres such as Expancel® (Nobel Industries), Polytrap® (Dow Corning) and silicone resin microbeads (Tospearl® from Toshiba), and the like.

The compositions of the invention may optionally include one or more agents that provide or enhance shine. Shine enhancing agents will typically have a refractive index greater than about 1.4, preferably greater than about 1.5 when measured as a film at 25° C. Suitable shine enhancing agents include without limitation, polyols, fatty esters, silicone phenylpropyldimethylsiloxysilicate, polybutene, polyisobutene, hydrogenated polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In one embodiment, the composition may comprise a shine-enhancing agent in an amount from about 0.1% to about 10% by weight, more typically from about 1% to about 5% by weight, based on the total weight of the composition.

The compositions of the invention may also comprise emollients and/or humectants. Suitable emollients include, without limitation, isopropyl myristate, petrolatum, volatile or non-volatile silicones oils (e.g., methicone, dimethicone), ester oils, mineral oils, hydrocarbon oils, and fatty acid esters. Suitable humectants include those such as polyols (e.g., glycols), including without limitation, glycerin, $C_{3-24}$ polyols such as propylene glycol, ethoxydiglycol, butylene glycol, pentylene glycol, hexylene glycol, caprylyl glycol, sugar alcohols, sorbitol, xylitol, and the like. Such components may be present, for example, in an individual or collective amount between about 0.001% to about 50% by weight of the composition.

Additional ingredients may be included in the compositions, optionally distributed in either or both phases of the emulsion, and comprise rheology modifiers, stabilizers, dispersants, active ingredients (e.g., collagenase inhibitors, elastase inhibitors, collagen stimulators, depigmenting agents, desquamating agents, etc.), preservatives, pH adjusters, colorants, fragrances, flavorants, anesthetics, anti-allergenics, antifungals, anti-inflammatories, antiseptics, chelating agents (e.g., EDTA and salts thereof), fragrances, lubricants, masking agents, medicaments, moisturizers, protectants, soothing agents, stabilizers, sunscreens (e.g., octyl-methoxycinnimate, avobenzene, etc.), antioxidants (e.g., BHT, TDPA, etc.), botanicals, surfactants, viscosifiers, vitamins, or any combinations thereof. Such components may be present, for example, in an individual or collective amount between about 0.001% to about 50% by weight of the composition.

The composition may comprise one or more preservatives or antimicrobial agents, such as methyl, ethyl, or propyl paraben, phenoxyethanol, and so on, in amounts ranging between about 0.0001% to about 5% by weight of the composition.

The compositions of the invention may be used in any kind of cosmetic or personal care formulation that can be applied to a human integument, and may be in the form of a liquid, a cream, a lotion, a solid stick, etc. For example, the cosmetic composition may be, without limitation, in the form of mascara, eye liner, lipstick, lip color, lip gloss, nail polish, foundation, concealer, and the like. Personal care products may include, for example, day creams or lotions, night creams or lotions, sunscreen lotions, creams, or oils and other SPF products, moisturizers, salves, ointments, gels, body milks, artificial tanning compositions, depilatories, etc. In some embodiments, the compositions are in the form of a mascara.

Methods for imparting high volume to the eyelashes comprise applying to the eyelashes a film of a mascara composition of the invention. In some embodiments, a plurality of coats are applied.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, § 201(i).

EXAMPLES

Example 1. Mascara Composition

A volumizing mascara composition of the invention was prepared according to the formula in Table 1. The mascara composition imparts high volume, color, and shine to the eyelashes while maintaining a fluid viscosity.

TABLE 1

| Ingredient | Percent |
|---|---|
| Demineralized Water | 44.50600 |
| Dimethicone/Silica/Sorb. Stear./PEG-40 Stear. | 0.21100 |
| Hydroxyethyl Cellulose | 0.15800 |
| Polyvinylpyrrolidone | 0.15800 |
| Sucrose Stearate | 1.05300 |
| Methylparaben | 0.40000 |
| Disodium EDTA | 0.20000 |
| Creatine | 0.10500 |
| Iron Oxides[1] | 7.10500 |
| D&C Black No. 2 | 0.26300 |
| Carnauba Wax | 4.73700 |
| Beeswax | 8.42100 |
| Paraffin Wax | 13.68400 |
| Ethylparaben | 0.20000 |
| Propylparaben | 0.19000 |
| POE (20M) Sorbitan Monoluarate | 0.78900 |
| Stearic Acid | 2.10500 |
| Cetyl Alcohol | 1.05300 |
| Isooctahexacontane | 0.26300 |
| Acrylates Copolymer/Isododecane | 0.78900 |
| Sodium Hydroxide Solution 50% | 0.54800 |
| Nylon-6 | 0.10500 |
| Silica/Eth.Methacrylate Copol/ITT | 0.26300 |
| Dimethicone-Visc.1.5 CST. | 1.05300 |
| Wheat Amino Acids | 0.10500 |
| Protein/Oligosacch Blend-Wheat | 0.10500 |
| Hydrolyzed Collagen | 0.10500 |
| Phenoxyethanol | 0.8000 |
| Acrylates/Ethylhexyl Acrylate Copolymer | 10.52600 |

[1]Surface coated with galactoarabinan

Microscopy on a thin film of the mascara reveals the presence of large lamellae in contrast to conventional oil-in-water mascaras, in which microscopy reveals predominantly micellar fractures.

Example 2. Rheology

Three mascara formulations (A, B, and C) were prepared with the ingredients shown in Table 2 below. Mascara A is a mascara of the invention, comprising sucrose stearate and high HLB emulsifiers (POE (20M) sorbitan monoluarate and cetyl alcohol). Mascara B was identical to Mascara A, except that it did not contain any sucrose stearate. Mascara C was also identical to Mascara A, except that it did not contain the high HLB emulsifiers, POE (20M) sorbitan monoluarate and cetyl alcohol. In each case, the water was adjusted to bring the total wt. % to 100%.

TABLE 2

| | Sample | | |
|---|---|---|---|
| | A | B | C |
| Ingredient | Wt. % | | |
| Demineralized Water | q.s. | q.s. | q.s. |
| Hydroxyethyl Cellulose | 0.15 | 0.15 | 0.15 |
| Sucrose Stearate | 1.00 | — | 1.00 |
| Carnauba Wax | 4.50 | 4.50 | 4.50 |
| Beeswax | 8.00 | 8.00 | 8.00 |
| Paraffin Wax | 13.00 | 13.0 | 13.00 |
| POE (20M) Sorbitan Monolaurate | 0.75 | 0.75 | — |
| Stearic Acid | 2.00 | 2.00 | 2.00 |
| Cetyl Alcohol | 1.00 | 1.00 | — |
| Sodium Hydroxide Solution 50% | 0.52 | 0.52 | 0.52 |
| Acrylates/Ethylhexyl Acrylate Copolymer-Aq. | 10.00 | 10.00 | 10.00 |

Samples A, B, and C were studied by obtaining stress sweep curves for each sample. FIG. 1 shows the increasing oscillatory stress in a rheometer and modulus G' as a function of oscillatory stress. As shown in FIG. 1, the mascara of the invention, Mascara A (○), has rheological properties comparable to a micellar composition (Sample C (□)) under low stress, but when subjected to higher stress, Mascara A showed properties comparable to a lamellar composition (Sample B (●)). These results demonstrate that depending on the oscillatory stress applied, mascaras of the invention may have rheological properties of both a micellar composition and a lamellar composition. The stress range of 1-100 (pa) is believed to correspond to the stresses encountered during application of a mascara.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

The invention claimed is:

1. A method of imparting high volume to eyelashes comprising applying to the eyelashes a film of a composition comprising:

an oil phase;
a water phase;
sucrose stearate emulsifier in an amount between about 0.1% and about 3% by weight; and
a high HLB emulsifier in an amount between about 0.1% and about 25% by weight, the high HLB emulsifier having an HLB value between about 15 and about 20;
wherein said composition is in the form of an oil-in-water emulsion comprising a lamellar and micellar phase;
wherein said composition comprises between about 10% and about 35% by weight wax, and has a viscosity of less than about 200,000 cps measured at a shear rate of 10 $s^{-1}$.

2. The method according to claim 1, wherein the high HLB emulsifier comprises polysorbate 20 and/or cetyl alcohol.

3. The method according to claim 1, wherein the wax is selected from the group consisting of carnauba wax, beeswax, paraffin wax, and combinations thereof.

4. The method according to claim 1, wherein the composition comprises between about 1% and about 3% by weight sucrose stearate and between about 0.5% and about 15% by weight high HLB emulsifier.

5. The method according to claim 1, wherein the composition further comprises a pigment.

6. The method according to claim 5, wherein the pigment comprises iron oxide.

* * * * *